US006183769B1

(12) United States Patent
Campbell et al.

(10) Patent No.: US 6,183,769 B1
(45) Date of Patent: Feb. 6, 2001

(54) METHODS OF ENHANCING REPRODUCTIVE PERFORMANCE OF ANIMALS

(75) Inventors: Roger Campbell, Corowa (AU); Erkki Virtanen, Helsinki (FI)

(73) Assignee: Cultor Ltd., Helsinki (FI)

( * ) Notice: Under 35 U.S.C. 154(b), the term of this patent shall be extended for 0 days.

(21) Appl. No.: 08/945,230

(22) PCT Filed: Apr. 19, 1996

(86) PCT No.: PCT/FI96/00211

§ 371 Date: Oct. 21, 1997

§ 102(e) Date: Oct. 21, 1997

(87) PCT Pub. No.: WO96/32850

PCT Pub. Date: Oct. 24, 1996

(30) Foreign Application Priority Data

Apr. 20, 1995 (AU) ................................... PN2507

(51) Int. Cl.[7] ........................................................ A23K 1/18
(52) U.S. Cl. .................................................... 424/438
(58) Field of Search ............................................. 424/438

(56) References Cited

U.S. PATENT DOCUMENTS 5,668,173 * 9/1997 Garrow ................................ 514/557

FOREIGN PATENT DOCUMENTS 9301144    1/1994  (BR) .
1-132533   11/1987  (JP) .

OTHER PUBLICATIONS

Steinmetzer, W. "Beitrag zur Biochemie und Verwendung des Ruberinhalsstoffs Betain", Zucker 1972, 25 (2) 48–57 Dialog Accession No. 00049403.

Weigland, E. et al "Betain– und Glutaminsaureanteile an der Stickstoffverdauung und–bilanz bei Vinassefutterung an Wachsende Schweine", Achiv fur Tiernahrung v. 31 (5/6), May 1981, pp. 335–343 Dialog Accession No. 1896246.

* cited by examiner

Primary Examiner—Carlos A. Azpuru
(74) Attorney, Agent, or Firm—Nixon & Vanderhye

(57) ABSTRACT

Reproductive performance and growth of non-human animals is enhanced by administering betaine to the animals. Betaine is administered to animals living under nutritional or lactational stress. Animal feeds for the enhancing of reproductive performance of animals contain betaine in addition to ingredients conventionally used in animal diets.

12 Claims, No Drawings

METHODS OF ENHANCING REPRODUCTIVE PERFORMANCE OF ANIMALS

This application is a 371 continuation of PCT/FI96/00211, filed Apr. 19, 1996 which is a continuation of Australian Patent No. PN2507, filed Apr. 20, 1995.

The present invention relates generally to animal husbandry and in particular to methods of improving or controlling the growth and/or reproduction of animals. More particularly, the present invention relates to methods of controlling stress and related conditions within animals during their growth and/or reproduction, particularly in the early stages of life of the animal, and more particularly when the animal is born in a litter. In a preferred embodiment, the present invention relates to controlling the growth of piglets and more typically to feeding sows with a stress regulator such as betaine, as part of a feed supplement, so that a significantly higher number of piglets are born alive than is considered usual in similar circumstances. Even more particularly, the present invention relates to the use of a stress regulator, particularly betaine, to control stress in sows so as to minimise stress during lactation which in turn increases the fertility and fecundity of the sows resulting in increases in the size of the litter to produce more living piglets, thus increasing productivity and reducing overhead costs. Other animals, to which the invention is applicable, include but are not limited to sheep, goat, cow, horse, cat, fur animals and poultry. In particular, the invention is useful for mammals suffering of lactational stress.

The present invention thus finds particular application in administering betaine or equivalent chemical compounds to animals in appropriate, predetermined dosages or amounts over or for an appropriate, predetermined time interval by administering the betaine separately or including the betaine in the feed of the animals during e.g. lactation to improve subsequent reproductive performance of the animal.

BACKGROUND OF THE INVENTION

The costs of keeping an animal breeding stock is considerable and for economic animal production it is essential for each parent to rear a large number of progeny.

By way of example, the number of piglets produced per sow is one of the key economical performance indicators in pig farming. With normal weaning, at three to four weeks, the aim should be for about 18 to 24 pigs to be reared per sow per annum, such as for example by having two litters of 9 to 12 piglets each. However, in practice, averages fall below these optimal figures due to (1) time being lost between weaning one litter and conception of the next, (2) many litters being born with too few pigs, and (3) a percentage, such as for example about 12%, of pigs being either stillborn or dying within the first few weeks of life. All of these result in a lower than optimal number of piglets surviving. The lower the number of piglets which survive and mature into pigs for meat production or breeding, the greater the cost to the farmer and the higher is the cost on a per pig basis of maintaining the herd, all of which contribute to a reduction in income for the farmer and a lowering of profits for the enterprise managing the pigs or similar.

Therefore, there is a need for management of the pig herd that allows a greater number of piglets to be born alive and survive to maturity than hitherto before was considered normal, as well as a need for piglets to develop faster and grow more quickly, and perhaps to have litters at a younger age and to have more piglets in a litter.

Betaine has been used in the past as a feed supplement for animals, but until recently, knowledge with regard to its role in animal metabolism has been sparse.

Betaine has recently been reported to both improve gut function and to increase the food intake and growth of animals. Betaine has also been found to decrease the body fat of for example fish, chicks, piglets and growing pigs [see e.g. Virtanen, E. et al., Effects of food containing betaine/amino acid additive on the osmotic adaption of young Atlantic salmon, *Salmo salar L.* Aquaculture 83 (1989) 109–122; Saunderson, C. L. and MacKinlay, J., Changes in body weight, composition and hepatic enzyme activities in response to dietary methionine, betaine and choline levels in growing chicks, British J. Nutrition 63 (1990)339–349; and Virtanen, E. and Campbell, R., Reduzierung der Rückenspeckdicke durch Einsatz von Betain bei Mastschweinen (Reduction of backfat thickness through betaine supplementation of diets for fattening pigs). Handbuch der tierischer Veredlung. Verlag H. Kamlage, Osnabrück, Deutschland, 19 (1994) 145–150]. Betaine has also been reported to have pharmacological effects. Thus, for example proline betaine has been reported to prevent perosis in chicks and glycine betaine has been reported to prevent the detrimental effects of coccidiosis in broilers (PCT/FI94/00166).

Until now, no investigations have been conducted to determine the effect of betaine on the reproduction of animals. It has now been surprisingly discovered that betaine, particularly when used in appropriate, predetermined amounts in feed stock, has resulted in significantly higher numbers of piglets in a litter being born alive. Even though betaine may have been used in the past in connection with pigs, the inventors have surprisingly discovered a hitherto before unknown property of the betaine. This property which has been newly discovered by the inventors relates to using betaine to achieve more fertile and fecund sows with the result that sows now have larger litters, particularly if the sows are fed betaine during lactation. As already stated, pigs are mentioned here by way of example, the invention being applicable to a large number of animals.

SUMMARY OF THE INVENTION

It is an object of the present invention to provide a method of enhancing the reproductive performance of an animal by administering an effective amount of betaine to the animal. Preferably, an effective amount of betaine is administered for a predetermined period of time during certain stages of the life of the animal, such as for example during lactation, gestation or other stress conditions.

A further object of the present invention is the use of betaine for the enhancement of the reproductive performance of an animal.

A still further object of the present invention is a diet for enhancing the reproductive performance of an animal, said diet comprising betaine in addition to ingredients conventionally used in animal feeds.

In connection with the present invention, the expression "reproductive performance" means the fertility and/or fecundity of the animal.

It is also an object of the present invention to provide a method of eliminating or reducing stress resulting in reduced reproductive performance of an animal by administering an effective amount of betaine to the animal.

Hence, according to the present invention there is provided a method of substantially eliminating or reducing stress in an animal, particularly a sow, comprising administering a predetermined amount of betaine to the animal for at least a predetermined time over a preselected period in order to effectively reduce or relieve stress, particularly nutritional stress.

DETAILED DESCRIPTION OF THE INVENTION

Betaine refers to fully N-methylated amino acids. Betaines are natural products that have an important function in the metabolism of both plants and animals. One of the most common betaines is a glycine derivative wherein three methyl groups are attached to the nitrogen atom of the glycine molecule. This betaine compound is called betaine, glycinebetaine or trimethylglycine.

Other betaines are for example alanine betaine and proline betaine and histidine betaine. R. G. Wyn Jones and R. Storey describe betaines in detail in *The Physiology and Biochemistry of Drought Resistance in Plants* (Paleg, L. G. and Aspinall, D. (Eds.), Academic Press, Sydney, Australia, 1981). The publication is included herein by reference.

Most organisms can synthesize small amounts of betaine for cell functions, such as methyl donor functions, but only a few accumulate betaine in high concentrations. Hence, betaine is not present in large quantities in most feedstuffs. Best known organisms accumulating betaine are plants belonging to the Chenopodiaceae family, for example sugar beet, and some microbes and marine invertebrates. The main reason for the betaine accumulation in these organisms is probably that betaine acts as an osmolyte and thus protects the-cells from the effects of osmotic stress. One of the main functions of betaine in these plants and microbes is to increase the osmotic strength of the cells when the conditions require this, for example in case of high salinity or drought, thus preventing water loss. Unlike many salts, betaine is highly compatible with enzymes, and the betaine content in cells and cell organelles may therefore be high without having any detrimental effect on the metabolism. Betaine has also been found to have a stabilizing effect on the operation of macromolecules; it improves the heat resistance and ionic tolerance of enzymes and cell membranes.

Betaine is thus a non-toxic natural product that does not have detrimental effects on plants or animals.

According to the present invention, betaine is used as a stress regulator for improving the fertility and fecundity of animals. Preferably, the betaine regulator is a glycine betaine (oxyneurin) or related compound. Even though this reference and the claims use the word 'betaine', it is clear that according to the invention several different betaines can be used, if desired. It should also be noted that betaine is used here as a general term which thus covers different known betaines. The word betaine hence includes proline betaine, β-alanine betaine, tryptophan betaine, histidine betaine, 2-mercaptohistidine betaine, homostachydrine (pipecolate betaine) and the like (see R. G. Wyn Jones and R. Stoney, supra, for reference)

Typically, the stress regulator of the present invention, which is particularly betaine or its equivalent forms, can be administered to any animal. Preferably, the animal is a non-human mammal. In a preferred embodiment, the animal is a pig and particularly a sow, more preferably a pregnant or lactating sow. Other animals include, but are not limited to, cow, sheep, horse, goat, dog, cat, fur animals, such as mink or fox, and poultry.

Typically, the betaine is administered alone or in combination with one or more other materials. Typically, the other materials include conventional feed compositions and additives such as wetting agents, other adjuvants, growth regulators, feed supplements, and the like. The other material can be added separately or in combination with the regulator. Even more typically, the regulator and other material have a synergistically beneficial effect on the animal.

Betaine can also be administered to the animal in the drinking water. Further, betaine can be administered separately from feed and drink intake, for example by oral administration or injection.

For the purpose of easy application and administration of the betaine, betaine can be purchased in appropriate storage packages containing crystalline betaine or solutions of betaine in appropriate solvents, such as water of salt solutions, for example. Betaine can also be included in commercial basal feeds, industrial feeds or feed supplements for different animals.

A diet suitable for the particular domestic food animal being raised is formulated using standard feed tables. For example, a standard diet for cattle may be formulated using the information provided by the Merck Veterinary Manual, sixth edition, pages 1104–1132 (1986), incorporated herein by reference. Using the same source, standard diets can be prepared for e.g. rabbits (pages 1210–1211); sheep (1211–1221); swine (pages 1221–1230); horses (1169–1185); and poultry (pages 1188–1210). Guidance with respect to suitable diets is also provided in the National Research Council's, U.S.A., Nutrient Requirements of Domestic Animals Series, incorporated herein by reference:

| | |
|---|---|
| Nutrient Requirements of Mink and Foxes, 1968 | 0-309-01676-2 |
| Nutrient Requirements of Trout, Salmon and Catfish, 1973 | 0-309-02141-3 |
| Nutrient Requirements of Dogs, 1974 | 0-309-02315-7 |
| Nutrient Requirements of Sheep, 1975 | 0-309-02212-6 |
| Nutrient Requirements of Beef Cattle, 1976 | 0-309-02419-6 |
| Nutrient Requirements of Rabbits, 1977 | 0-3Q9-02607-3 |
| Nutrient Requirements of Warmwater Fishes, 1977 | 0-309-02616-1 |
| Nutrient Requirements of Poultry, 1977 | 0-309-02735-X |
| Nutrient Requirements of Cats, 1978 | 0-309-02343-8 |
| Nutrient Requirements of Horses, 1978 | 0-309-02760-8 |
| Nutrient Requirements of Dairy Cattle, 1978 | 0-309-02749-7 |
| Nutrient Requirements of Nonhuman Primates, 1978 | 0-309-02786-1 |
| Nutrient Requirements of Laboratory Animals, 1978 | 0-309-02767-5 |
| Nutrient Requirements of Swine, 1979 | 0-309-02870-1 |
| Nutrient Requirements of Coldwater Fishes, 1981 | 0-309-03187-7 | and later, revised editions.

The publications are available from the National Academy Press, 2101 Constitution Avenue, N.W., Washington D.C. 20418, U.S.A. The standard diet is supplemented with from 0.01% to 0.5% betaine (by weight) and preferably with 0.1% to 0.3% betaine (by weight). The diet comprised of standard feedstuffs supplemented with an optimum percentage of betaine for improving fertility and/or fecundity, is encompassed by the present invention.

The amount of betaine used varies depending on the animal, its health and particular growth and stress conditions. A useful amount may be for example about 0.1 to 10 kg of betaine per tonne of feed administered. A preferable amount is thus for example about 1 to 4 kg of betaine per tonne of feed. Typically, the feed administered to a sow contains up to 4.0 kg/tonne or more, more typically from 1.0 to 3.0 kg/tonne and preferably 2.0 kg/tonne of betaine or equivalent compound. The amounts given here are only suggestive; the scope of the present invention thus contains all amounts that work in the manner described herein.

Typically, the stress induced or developed in the animals includes nutritional stresses such as, for example, stress related to an inadequate intake of amino acids and other nutrients relative to the animal's tissue demands and its use of nutrients for functions other than lactation or maintenance of the animal's body composition, which in turn results in reduced milk production and impaired subsequent fertility and fecundity.

Lactating animals, such as sows used for feeding piglets, particularly in the piglets' first few weeks of life, are always under considerable nutritional and other stress. However, the nature of, causes of and reasons for the nutritional stress are not entirely understood at present. The present invention shows that the administration of betaine to animals at certain times, particularly during nutritional stress, such as lactation, results in cost effective improvements in subsequent fertility or fecundity, particularly fecundity in that the sows have larger litters.

The present invention will now be described by way of example with reference to the following examples.

Although the present invention in the examples will be described with particular reference to the use of glycine betaine, as one example of a regulator or other additive or feed supplement, administered to sows to effect significantly higher numbers of piglets born alive in litters, it is to be noted that the scope of the present invention is not restricted to the described embodiments, but rather the present invention is more extensive so as to include the use of other regulators, to other ways of administering the regulators, and to other use of the chemical compounds than as regulators as described, and to the use of the regulators on animals other than those specifically described, and to the use of chemical compounds other than betaine.

In the examples, as well as in the general description and the claims, tonne refers to metric tonne.

EXAMPLE 1

The experiment was conducted to investigate the effect of four levels of dietary betaine (0, 1.0, 2.0 and 4.0 kg/tonne) on the lactational and subsequent reproductive performance of gilts (which are young female pigs) and of older parity sows.

Twenty gilts (denoted as parity group P1 in Table 1) and 20 older parity sows (denoted as parity group P2 in Table 1) were allocated to each of the treatments as described below over a four week period. The treatments consisted of feeding or providing the sows with a conventional lactation diet of the following composition, containing about 14.0 megajoules (MJ) of digestible energy per kg and about 0.85% lysine, or the same diet supplemented with the previously described levels of betaine.

| BMI lactation, Formula 9263 | | | |
|---|---|---|---|
| Raw Material | % | Kg | Tonnes |
| 1 Wheat 11% | 44.9333 | 1348.000 | 125.541 |
| 12 Barley 10.5% | 18.0000 | 540.000 | 50.291 |
| 110 Lupin Kernels 34% | 4.0000 | 120.000 | 11.176 |
| 200 Millmix | 10.1333 | 304.000 | 28.312 |
| 325 Soyabeanmeal 48% | 10.5000 | 315.000 | 29.336 |
| 400 Meatmeal | 6.9667 | 209.000 | 19.464 |
| 410 Fishmeal 67% | 1.0000 | 30.000 | 2.794 |
| 500 Water | 1.0000 | 30.000 | 2.794 |
| 520 Tallow-Mixer | 2.5333 | 76.000 | 7.078 |
| 550 Salt | 0.2000 | 6.000 | 0.559 |

-continued

| BMI lactation, Formula 9263 | | | |
|---|---|---|---|
| 560 Limestone | 0.6000 | 18.000 | 1.676 |
| 708 BMI Breeder PMX | 0.1500 | 4.500 | 0.419 |

| Analysis | | | |
|---|---|---|---|
| [Volume]: | 100.0000 | *ALY/DE-: | 0.8502 |
| [Drymat]: | 89.5422 | *MET/LYS: | 0.3138 |
| DE-Pig: | 14.0251 | *M + C/LYS: | 0.6770 |
| NE-Pigs: | 9.8205 | *THR/LYS: | 0.7351 |
| *LYS/NE-: | 0.0908 | *ISO/LYS: | 0.8122 |
| *ALY/NE-: | 0.0718 | *TRY/LYS: | 0.2400 |
| Protein: | 18.8427 | Salt: | 0.4144 |
| Fat: | 5.4423 | Linolein: | 1.0697 |
| Fibre: | 3.4909 | % Legumes: | 3.9914 |
| Ash: | 5.6732 | ABC: | 678.6763 |
| Calcium: | 1.0086 | Poult.ME: | 11.8020 |
| T. Phos: | 0.7364 | Rumin.ME: | 12.1318 |
| Av. Phos: | 0.4913 | Sodium: | 0.1503 |
| Lysine: | 0.8915 | Potass: | 0.6435 |
| Alysine: | 0.7047 | Chloride: | 0.2511 |
| Methion: | 0.2797 | Magnes: | 0.1514 |
| M + C: | 0.6835 | Na + K − Cl: | 158.3466 |
| Threo: | 0.6553 | Bulkdens: | 59.3973 |
| Isoleuc: | 0.7240 | Choline: | 1327.5338 |
| Trypto: | 0.2185 | Interfat: | 5.4423 |
| *LYS/DE-: | 0.0636 | | |

Instead of this diet, any other appropriate diet for lactating sows, including about 13.0 MJ/kg to 15.0 MJ/kg of digestible energy and about 0.75 to 1.2% lysine, can be used. The treatments (diets) were given the following descriptions:

CL0 Control lactation diet, containing no betaine
CL1 Control lactation diet plus 1.0 kg of betaine per tonne in the feedstock provided to the sows
CL2 Control lactation diet plus 2.0 kg betaine per tonne in the feedstock provided to the sows
CL4 Control lactation diet plus 4.0 kg betaine per tonne in the feedstock provided to the sows.

All diets were offered ad libitum to the sows during lactation. Milk production of the sows as a consequence of being provided with the diet was assessed on the basis of piglet growth rate from day 2 after birth through to weaning of the piglet at 24 days of age.

All fostering of the piglets occurred within the first two days after birth when the various litter sizes were standardised at 10 for gilts (parity group P1) and 11 (if possible) for older sows, for each gilt or sow respectively. Litter weight was also recorded at day 2 and again at weaning. The gilts (P1) were also fed the conventional lactation diet at 3.0 kg/d (twice daily) from the time of weaning to the time of remating and were mated at their first oestrus after weaning.

Weaned sows were fed a gestation diet containing 13.0 MJ digestible energy per kg and 0.6% lysine at 2.5 kg/d from weaning to remating and mated at their first oestrus after weaning.

The subsequent fertility (farrowing rate) and fecundity (litter size) of all sows were recorded.

Lactational performance was not observed to be affected by betaine at levels from 1.0 to 2.0 kg/tonne but a slight reduction in piglet growth rate was observed when the diet was supplemented with 4.0 kg/tonne of betaine. The latter was associated with, and probably caused-by, a reduction in sow feed intake.

Increasing the level of supplementary betaine in the diet from 0 through 1.0 kg/tonne to 2.0 kg/tonne resulted in no observable effect being demonstrated on sow feed intake; on piglet growth rate or on total litter weight at the time of weaning and further there were no significant interactions between the effects of parity and amount of betaine for any parameter measured.

The results of subsequent reproductive performance of the sows treated with the different diet treatments are provided in Table 1 which shows a tendency for gilts offered the diet supplemented with 4.0 kg betaine/tonne during lactation to have a lower farrowing rate than those on the other three diet treatments. The difference, however, did not approach significance. Otherwise, farrowing rates were similar for gilts and older parity sows.

Total litter size was higher for older parity sows than gilts and was affected by a significant interaction between the effects of parity and betaine. The latter results showed that the number of total piglets born was higher for gilts offered the diet containing 2.0 kg betaine/tonne and lower for older sows offered the diet containing 4.0 kg supplementary betaine/tonne during their previous lactation.

Similar differences between treatments existed for piglets born alive except that there was no interaction between the effects of parity and betaine. Both gilts and older parity sows offered the diet containing 2.0 kg supplementary betaine/tonne during lactation had significantly more piglets born alive than those offered the control diet or the diet containing 4.0 kg supplementary betaine/tonne (Table 1). Still birth percentage was higher for older parity sows compared to gilts and was unaffected by betaine (P=0.652).

Thus, it can be readily seen that administering betaine in selected dosages to sows, particularly during lactation, results in significant increases in fertility and fecundity of sows.

TABLE 1

Effects of the level of supplementary betaine offered gilts (P1) and older parity sows (P2) during lactation on subsequent reproductive performance

| Parity | Betaine kg/tonne) | Farrowing rate (%) | Total born | Born alive | SPB[1] |
|---|---|---|---|---|---|
| 1 | 0 | 89.0 | 10.15 | 9.92 | 1.98 |
|   | 1.0 | 94.0 | 9.70 | 9.10 | 6.40 |
|   | 2.0 | 91.1 | 11.08 | 10.83 | 2.43 |
|   | 4.0 | 83.0 | 9.85 | 9.00 | 6.19 |
| 2 | 0 | 89.1 | 11.93 | 10.29 | 12.61 |
|   | 1.0 | 89.0 | 12.27 | 10.87 | 10.88 |
|   | 2.0 | 95.0 | 12.71 | 11.64 | 8.30 |
|   | 4.0 | 94.0 | 11.00 | 9.93 | 8.96 |
| Significance p = | | | | | |
| Parity (P) | | .735 | .001 | .026 | .001 |
| Betaine (B) | | .821 | .652 | .027 | .652 |
| P × B | | .683 | .001 | .699 | .427 |

[1]Still birth percentage

EXAMPLE 2

To further investigate the positive effects of betaine on the litter size, the experiment described in Example 1 was repeated, but in this experiment a total of 150 sows were fed a standard diet supplemented with 0 or 2.0 kg betaine/tonne during lactation.

The results are provided in Table 2.

TABLE 2

The interrelationship between parity and betaine during lactation on the subsequent litter size of sows

| Parity | Betaine (kg/t) | Total born | Born alive |
|---|---|---|---|
| 1 | 0 | 12.0 | 10.7 |
|   | 2.0 | 12.0 | 10.9 |
| 2 | 0 | 10.2 | 9.5 |
|   | 2.0 | 12.5 | 12.3 |
| Significance | | | |
| Parity (P) | | .332 | .983 |
| Betaine (B) | | .215 | .048 |
| P × B | | .148 | .022 |

Betaine did not have any significant effects on piglet growth rate or sow feed intake during lactation. However, betaine had a very favorable effect both on the size and the health of the litter. The effect on litter size during subsequent reproduction was significant at the 5% level. There was also a significant interaction between the effects of betaine and parity for litter size; the response being greatest in older sows. This is probably indicating that betaine has the biggest effect when the litter size is relatively low. On the basis of the results, it seems that events during lactation have a major influence on subsequent litter size. In particular, the results indicate that betaine alleviates tissue changes which normally lead to reduced reproductive performance. Hence, betaine is effective in improving the reproductive performance of animals, and particularly effective during periods of lactational stress, such as summer and early weaning. Furthermore, the favorable effects of betaine tend to increase with increasing age of the animals, thus making it possible to secure the reproductive performance of the animals for a longer period of time.

The described invention has been advanced by explanation and many modifications may be made without departing from the spirit and scope of the invention which includes every novel feature and novel combination of features hereindisclosed.

Those skilled in the art will appreciate that the invention described herein is susceptible to variations and modifications other than those specifically described. It is understood that the invention includes all such variations and modifications which fall within the spirit and scope.

What is claimed is:

1. A method of enhancing the reproductive performance of a non-human animal comprising administering to said animal an effective amount of betaine.

2. A method of enhancing the fecundity of a non-human animal comprising administering to said animal an effective amount of betaine.

3. A method of reducing nutritional, gestational or lactational stress in a non-human animal comprising administering to said animal an effective amount of betaine.

4. The method according to any one of claims 1, 2 or 3 wherein the betaine is administered alone, in the animal's feed or in the animal's drinking water.

5. The method according to claim 4 wherein the betaine is administered in an amount of 0.1 to 10 kg of betaine per metric tonne of feed.

6. The method according to claim 5 wherein the animal's feed contains 1 to 4 kg of betaine per metric tonne of feed.

7. The method according to claim 6 wherein the animal's feed contains 1 to 3 kg of betaine per metric tonne of feed.

8. The method according to any one of claims 1, 2 or 3 wherein the non-human animal is a sheep, cow, horse, goat, fur-bearing animal, cat, dog or poultry.

9. The method according to claim 8 wherein the animal is a pig.

10. The method according to claim 3 wherein the animal is subject to gestational stress.

11. The method according to claim 3 wherein the animal is subject to lactational stress and the betaine is administered to the animal during lactation.

12. A method of enhancing fecundity and progeny of a non-human animal comprising administering to said animal an effective amount of betaine.

* * * * *